May 16, 1967 E. S. BOERNER Plant Pat. 2,741
CHRYSANTHEMUM PLANT
Filed May 17, 1966
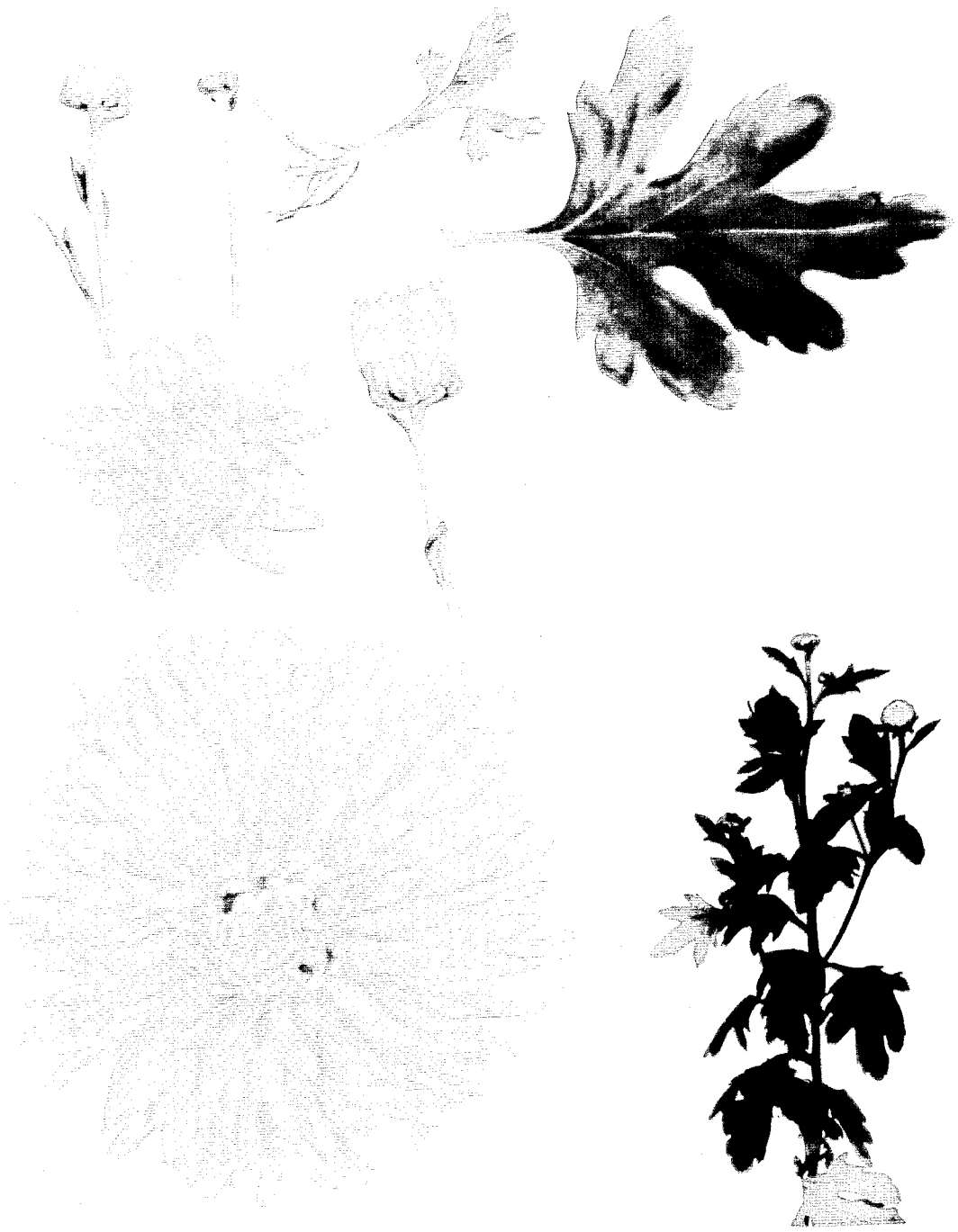
Inventor.
E. S. Boerner
By: Robb & Robb
Attorneys.

United States Patent Office

Plant Pat. 2,741
Patented May 16, 1967

2,741
CHRYSANTHEMUM PLANT

Eugene S. Boerner, Newark, N.Y., assignor to Jackson & Perkins Company, Newark, N.Y., a corporation of New York Filed May 17, 1966, Ser. No. 550,874
1 Claim. (Cl. Plt.—81)

The present invention relates to a new and distinct variety of Chrysanthemum plant of the thick decorative class, which was originated by me as a selfed seedling of the variety known as "Purple Finch" (Plant Patent No. 2028).

The primary objective of this breeding was to produce a new and improved chrysanthemum variety having the strong plant habit of the parent variety and which bears large flowers in the color range of those of the parent. This objective was fully achieved, as evidenced by the following unique combination of characteristics which are outstanding in the new variety and which distinguish it from its parent, as well as from all other varieties of which I am aware:

(1) A strong and upright habit of growth;
(2) A free blooming habit;
(3) A large flower size;
(4) A thick flower form; and
(5) A distinctive and attractive general color tonality of the flowers corresponding to Spinel Red, lightly overcast with Tyrian Rose.

Asexual reproduction of the new variety by both top cuttings and underground runners, as performed at Newark, N.Y., shows that the foregoing characteristics and distinctions come true to form and are established and transmitted through succeeding propagations.

The accompanying drawings shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Selfed seedling.
*Seed parent.*—"Purple Finch."
*Pollen parent.*—"Purple Finch."
Classification: Thick; decorative.
Growth: Grows 24 inches tall.
Location where observations made: In the field at Newark, N.Y. in the early morning during the first part of the month of October.
Cold resistance: Winter hardy in northern New York State.
Blooming period: In Newark, N.Y. climatic area, runs from September until frost.

*Flower*

Bud:
*Color.*—When petals first divide—Spinel Red, Plate 26. When petals begin to unfurl—Pomegranate Purple, Plate 12, very lightly overcast with Rose Red, Plate 12. When half blown: inside—Rose Red, Plate 12, very lightly overcast with Pomegranate Purple, Plate 12; outside—Spinel Red, Plate 26, lightly overcast with Rose Red, Plate 12.
*Peduncle.* — Color — Courge Green, Plate 17. Strength—strong.

Bloom:
*Size.*—6 inches.
*Stem.*—Stiff.
*Form.*—Decorative; thick.
*Petalage.*—Very double.
*Color.*—Center of flower—Pomegranate Purple, Plate 12, with center of petal very lightly overcast with Tyrian Rose, Plate 12. Outer petals—Spinel Red, Plate 26, very lightly overcast with Spinel Pink, Plate 26 at the tip end of petal. Base of petals—Light Turtle Green, Plate 32. Inside of petals—Spinel Red, Plate 26, very lightly overcast with Tyrian Rose, Plate 12. Reverse of petals—Pomegranate Purple, Plate 12, lightly overcast with Rosolane Purple, Plate 26.
*Petals.*—Texture—thick. Form—oval pointed.
*Fragrance.*—Characteristic chrysanthemum.

*Plant*

Form: Upright; branching.
Growth: Very free.
Foliage:
*Size.*—Large.
*Quantity.*—Normal.
*Color.*—Upper side—Varley's Green, Plate 18. Reverse side—Light Elm Green, Plate 17.
*Texture.*—Leathery.

I claim:

A new and distinct variety of Chrysanthemum plant of the thick decorative class, substantially as herein shown and described, characterized particularly as to novelty by the unique combination of a strong and upright habit of growth, a free blooming habit, a large flower size, thick flower form, and distinctive and attractive general color tonality of the flowers corresponding to Spinel Red, lightly overcast with Tyrian Rose.

No references cited.

ABRAHAM G. STONE, *Primary Examiner.*
ROBERT E. BAGWILL, *Examiner.*